United States Patent [19]
Zhang

[11] Patent Number: 5,616,400
[45] Date of Patent: Apr. 1, 1997

[54] COLD SEAL ADHESIVES, COLD SEALABLE FILMS AND PACKAGES FORMED THEREWITH

[75] Inventor: Tianhong Zhang, Columbus, Ohio

[73] Assignee: Century International Adhesives & Coating Corporation, Ohio

[21] Appl. No.: 559,844

[22] Filed: Nov. 20, 1995

[51] Int. Cl.$^6$ .................................................. C09J 7/02
[52] U.S. Cl. ........................ 428/195; 428/198; 428/906; 428/355 N; 524/591; 524/839; 524/840
[58] Field of Search ...................... 428/195, 198, 428/355, 906; 524/591, 839, 840

[56] References Cited

U.S. PATENT DOCUMENTS

| | | | |
|---|---|---|---|
| 4,240,942 | 12/1980 | Wenzel | 524/591 |
| 4,540,633 | 9/1985 | Kucera | 524/591 |
| 4,623,416 | 11/1986 | Henning | 524/591 |
| 4,851,459 | 7/1989 | Ramalingam | 524/591 |
| 4,859,521 | 8/1989 | Pike | 428/195 |
| 4,861,826 | 8/1989 | Hummerich | 524/839 |
| 4,889,884 | 12/1989 | Dust | 524/314 |
| 4,902,370 | 2/1990 | Dust | 524/314 |
| 5,334,690 | 8/1994 | Schafheutle | 528/71 |
| 5,486,426 | 1/1996 | McGee | 428/355 |

*Primary Examiner*—Jenna Davis
*Attorney, Agent, or Firm*—Carroll F. Palmer

[57] ABSTRACT

Cold-seal adhesives are disclosed that contain no natural rubber and are capable of forming dry coatings on flexible films which adhere to one another with commercially acceptable packaging strength at room temperature by pressure contact, but also allow such layered substrates to be reeled into rolls and stored for extended periods of time without blocking. The flexible films are usable in forming packages, particularly for comestibles and pharmaceuticals, without need for heat sealing. Such cold-seal adhesives are aqueous dispersions having a Zahn Cup #2 viscosity between 16–40 seconds containing 30 to 50 percent solids content of a polyurethane ionomer reaction product of 50–80% polyester polyol, 15–25% aliphatic diisocyanate and 3–6% dimethylol propionic acid neutralized with a base selected from tertiary amines and alkali metal hydroxides and the reaction product possesses a $T_g$ of between about $-20°$ to $5°$ C.

5 Claims, 1 Drawing Sheet

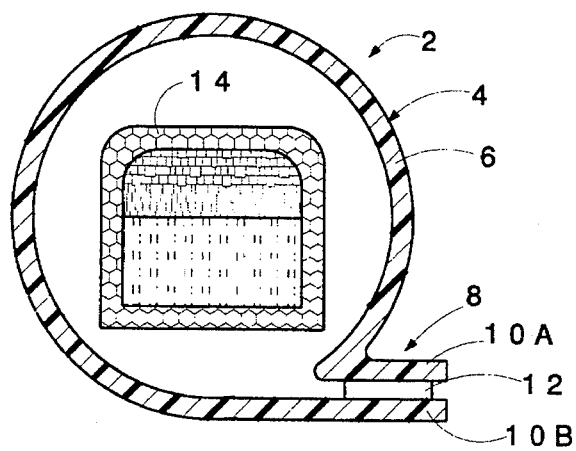
F I G. 1
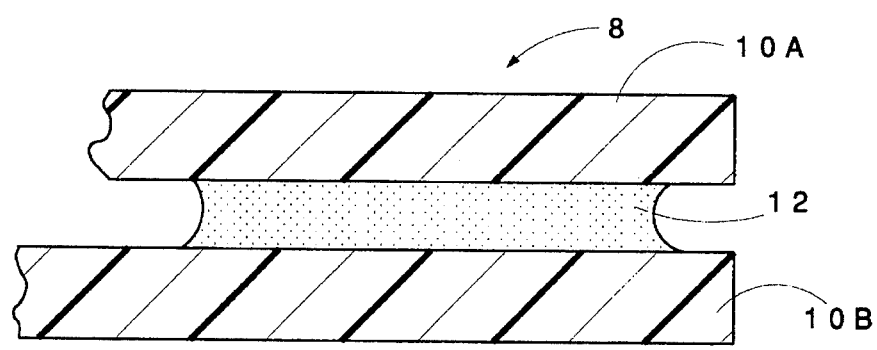
F I G. 2
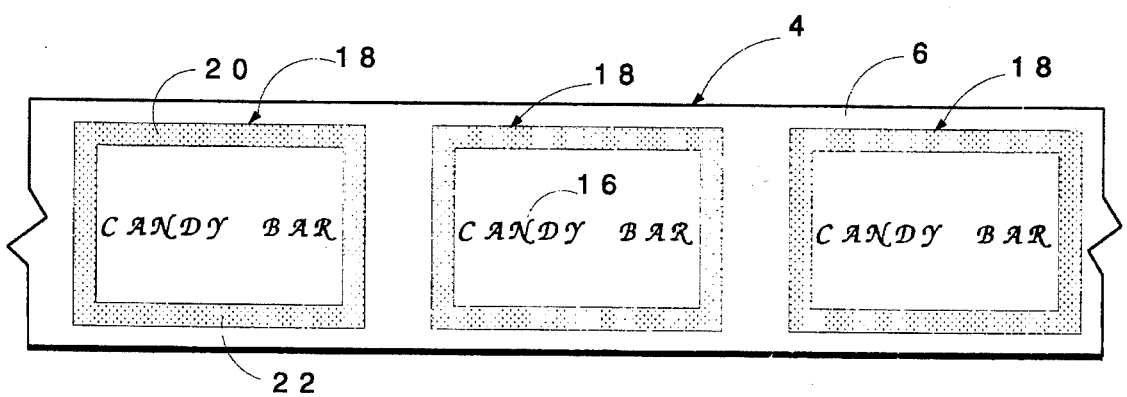
F I G. 3

COLD SEAL ADHESIVES, COLD SEALABLE FILMS AND PACKAGES FORMED THEREWITH

BACKGROUND OF THE INVENTION

1. Field of the Invention

This application relates broadly to cold-seal adhesives, cold-sealable films, methods of forming packages therewith and packages sealed with the new cold-seal adhesives. More particularly, it concerns (a) polyurethane containing aqueous dispersion adhesives capable of forming dry, non-blocking adhesive layers on plastic film or equivalent webs that can then later be pressure bonded together without use of heat, (b) cold-sealable packaging films comprising such adhesive layers and (c) packages formed and sealed with such packaging films.

2. Description of the Prior Art

Cold-seal adhesives are an established class of commercial adhesives characterized by being coated onto plastic films or other substrates to form layers that have the capability of strongly bonding to themselves when pressure is applied, but lacking adhesion to low energy surfaces, e.g., plastic films, coated papers, etc., so such flexible webs bearing these cold-seal adhesives layers may be formed into rolls without blocking, i.e., without sticking together. The technical literature contains information about cold-seal adhesives which have become a recognized commercial commodity, e.g., see U.S. Pat. Nos. 4,810,745, 4,859,521, and 4,902,370.

Natural rubber remains a major component of choice for the production of cold-seal adhesives in spite of disadvantages associated with natural rubber latex, including age discoloration, unpleasant odor, undesirable foaming in wet form and possibility of anaphylactic shock due to presence of natural latex proteins. To overcome the problems associated with natural rubber, synthetic polymer dispersions have been used to replace it in cold-seal adhesive formulations as shown by U.S. Pat. Nos. 4,889,884 & 4,902,370. While limited success has been accomplished in mitigating the aforementioned problems, the fundamental balance of satisfactory cohesive bond strength vs antiblocking properties desired in cold-seal adhesives has proven hard to achieve on a commercial basis without use of natural rubber.

The present invention provides new forms of cold seal adhesives with remarkable balance of satisfactory cohesive bond strength vs antiblocking properties without use of natural rubber as an essential component.

Aqueous polyurethane dispersions are a known class of polymer systems as are various methods for their production and their use as coatings and adhesives, as shown by U.S. Pat. Nos. 4,623,416 & 4,851,459. The present invention builds on this prior knowledge to advance the art in production of cold-seal adhesives and their utilization in cold-sealable packaging films plus packages made therefrom and sealed without recourse to heat sealing.

OBJECTS

A principal object of the invention is the provision of new forms of polyurethane based, aqueous dispersions capable of forming cold-seal adhesive layers on substrates that possess a commercially acceptable balance of cohesiveness and antiblocking quality.

Further objects include the provision of:

1. Unique methods for production of such polyurethane based, aqueous dispersions.

2. Cold-seal adhesives in the form of aqueous dispersions that are devoid of problems associated with known cold-seal adhesives based on natural rubber latex.

3. Such cold-seal adhesives which in the form of a dry layer exhibit excellent antiblocking properties toward low energy plastic films or like webs, but still are capable of forming a strong cohesive bond between themselves under commercially acceptable pressure application.

3. New forms of cold-sealable packaging films.

4. New forms of packages formed from packaging film without use a heat sealing and characterized by absence of anaphylactic proteins and other substances prohibited by governmental regulations on the packaging of comestibles and pharmaceuticals.

5. Unique adhesive aqueous dispersions that can be compounded with commercially available aqueous dispersions including acrylic polymer dispersions, vinyl polymer dispersions, synthetic elastomer dispersions, tackifiers, antiblocking agents, etc. to enhance specific properties or requirements.

Other objects and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

SUMMARY OF THE INVENTION

The objects are accomplished in accordance with the invention by the provision of a cold-seal adhesive composition in the form of an aqueous dispersion having a Zahn Cup #2 viscosity between 16–40 seconds containing 30 to 50 percent solids content of a polyurethane ionomer reaction product of 50–80% polyester polyol, 15–25% aliphatic diisocyanate and 3–6% dimethylol propionic acid neutralized with a base selected from tertiary amines and alkali hydroxides. The reaction product possesses a $T_g$ of between about −20° to 5° C.

The invention further provides unique sheet material for packaging of comestibles and pharmaceuticals comprising a continuous flexible plastic film having a surface energy level above 36 dynes/cm bearing a geometric pattern coating of dry cold seal adhesive consisting essentially of a polyurethane ionomer as described above. The opposite surface of the film has a surface energy level below 32 dynes/cm.

Additionally, the invention provides packages of items, especially comestibles and pharmaceuticals, comprising an envelope of flexible plastic film as described above having overlapping coatings of the cold seal adhesive pressure sealed together.

Polyester polyols used in accordance with the invention are commercially available polyester polyols per se or with an optional minor amount of polyether polyol, namely, a mixture containing about 0–20% polyether polyol and 80–100% polyester polyol, used in forming the polyurethane ionomer reaction product.

Preferred polyester polyols include the condensation products of diethylene glycol or dipropylene glycol with adipic acid or adipic acid with an optional amount of phthalic acid (up to 30% based upon the total weight of the mixture), e.g., poly(diethylene glycol adipate). Their average molecular weights range from 500 to 4000, especially 1000–3000.

Preferred polyether polyols include polypropylene glycol and ethylene oxide end capped polypropylene glycol with an average molecular weight from 500 to 4000, especially 1000–3000.

Preferred diisocyantes include hydrogenate methylene dihpenyl diisocyante (HMDI), hexamethylene diisocyanate (HDI), and, especially, isophorene diisocyanate (IPDI).

Preferred neutralization bases include triethanolamine, triethylamine and potassium hydroxide. The mechanical strength of the dry cold-seal adhesive films (coatings) of the invention varies with the base used for neutralization with KOH yielding the strongest films.

The aqueous dispersions of polyurethane prepolymers formed as precursors to the adhesive polyurethane ionomer reaction products of the invention are chain extended with water or the combination of water and a multifunctional aliphatic amine chain extender with 2–4 primary and secondary nitrogen atoms and 2–20 carbon atoms. Such amine chain extenders include ethylene diamine, 1,4-butanediamine, isophorene diamine, triethylenetetraamine, and triethylene oxide diamine (Huntsman EDR 148). Preferably, the quantity of the chain extender reagent is between about 0 to 2% of the total quantity of components used to form the polyurethane ionomer.

In preferred embodiments, the cold seal adhesive coating in the new packaging films is the dried residue from the gravure roll application to the film of an aqueous cold seal adhesive dispersion as described above. Advantageously, the pattern of the coating consists of stripes of the cold-seal adhesive, particularly stripes in the form of a plurality of separate rectangles spaced apart longitudinally along the film.

Important new products of the invention are non-blocking rolls of sheet material for packaging of comestibles and pharmaceuticals comprising a continuous flexible plastic film having a side with a surface energy level above 36 dynes/cm bearing a geometric pattern coating of dry cold seal adhesive as described above. The opposite side of such cold seal adhesive coated film advantageously has a surface energy level below 32 dynes/cm.

Typically, the new polymer systems of the invention, when used as adhesives, are applied, e.g., by use of a gravure cylinder, in controlled stripe patterns to a film, foil or other flexible substrate having a surface energy value above 36 dynes/cm to give a dry coating weight of about 1 to 4 lb., especially 2–3 lb., per 3000 square feet of substrate surface. Such adhesive coated substrates after thorough drying can be rolled up for storage and transportation without blocking. Eventually, such coated substrates can be sealed together by overlapping the stripe patterns of dry adhesive and applying pressure to give good contact with formation of cohesive bonding between the cold-seal adhesive stripes.

BRIEF DESCRIPTION OF THE DRAWINGS

A more complete understanding of the invention can be obtained by reference to the accompanying drawings in which generic parts of the illustrated matter are indicated by arrowhead lines associated with the designation numerals while specific parts are indicated with plain lines associated with the numerals and wherein:

FIG. 1 is a sectional view of a package formed in accordance with the invention.

FIG. 2 is a fragmentary sectional view of a package seal formed using cold-sealable plastic packaging film of the invention.

FIG. 3 is a fragmentary plan view of a cold-sealable plastic packaging film provided in accordance with the invention.

A package 2 of the invention comprises a wrapper 4 of plastic film 6 having longitudinal closure 8 which is formed of abutted film portions 10A and 10B sealed together by the adhesive layer 12 enclosing the comestible 14.

The creation of the final package 2 begins with a wrapping material 4 comprising plastic film 6 having applied thereto artwork 16 and a layer of cold seal adhesive 18 of the invention typically in a rectangular pattern defined by longitudinal stripes 20 and transverse stripes 22.

DESCRIPTION OF THE PREFERRED EMBODIMENTS

This invention is illustrated by the following examples of production of cold-seal adhesives and their utilization in accordance therewith. Such examples are for the purpose of illustration and are not intended to limit the scope of the invention unless otherwise specifically indicated. In these examples and throughout the remainder of this specification and the appended claims, all parts are by weight and all percentages are by weight of the total weight of all combined components.

EXAMPLE 1

To a heat-jacketed reactor equipped with agitator, temperature controller and nitrogen in/outlet, 300 parts of poly-(diethylene glycol adipate) (Ruco S-1011-55, hydroxyl no. 55), 69.4 parts of isophorene diisocyanate (IPDI, Huls) and 0.1 part of dibutyltin dilaurate are charged under nitrogen purge. This reaction mixture is heated to 85° C. and stirred for one hour, followed by the addition of 13.4 parts of dimethylol propionic acid and 0.1 part of dibutyltin dilaurate. The reaction is then continued at 85° C. for another 5 hours to reach a NCO content about 1.5%. At such point, heating is stopped and 10.1 parts of triethylamine amine is added to the reactor with stirring continued for 10 minutes to neutralize the viscous, anhydrous reaction product. Then, 600 parts of water is added to the reactor with vigorous stirring over a period of 30 minutes forming an aqueous dispersion of the polyurethane ionomer. Final stirring for two hours yields a bluish color, translucent aqueous dispersion containing about 40% solids with a pH of 7.5 and a Zahn No. 2 cup viscosity of 20 seconds.

EXAMPLE 2

To a heat-jacketed reactor equipped with agitator, temperature controller and nitrogen in/outlet, 300 parts of Ruco S-1022-55, 74.9 parts of isophorene diisocyanate (IPDI, Huls) and 0.1 part of dibutyltin dilaurate are charged under nitrogen purge. This reaction mixture is heated to 85° C. and stirred for one hour, followed by the addition of 16.1 parts of dimethylol propionic acid and 0.1 part of dibutyltin dilaurate. The reaction is then continued at 85° C. for another 5 hours to reach a NCO content about 1.6%. At such point, the viscous polymer melt is transferred to 600 parts of water containing 17.8 parts of triethanolamine under vigorous stirring for 30 minutes to form an aqueous dispersion. Then, 4.5 parts of triethylene oxide diamine (Huntsman EDR 148) is added to the dispersion and stirring is continued for another two hours. The final aqueous ionomer dispersion is milky white in color containing about 40% solids with a pH of 7.7 and a Zahn No. 2 cup viscosity of 30 seconds.

EXAMPLE 3

The dispersion of Example 1 is coated on three different substrates on a gravure coating cylinder to get a dry coat weight of 2.0 lb./ream. The substrates are:

| Substrate | Coated Side Surface Energy | Uncoated Side Surface Energy |
|---|---|---|
| A - Toray PC-1 film A | 38 dynes/cm | 32 dynes/cm |
| B - Toray PC-1 film B | 38 dynes/cm | 30 dynes/cm |
| C - Mobil 60-Mac film | 38 dynes/cm | 32 dynes/cm |

Substrates A, B & C are laminates of a film of treated oriented polypropylene on the coated side and untreated oriented polypropylene on the uncoated side. Additionally, substrate B has polyamide lacquered surface on the untreated polypropylene.

The applied fluid coating is oven dried at a temperature range of 90°–95° C. following which the resulting dry coated films are rolled into firm rolls for blocking and cold seal evaluation conducted immediately after roll formation and after aging at 25° C. for one month.

Blocking is measured as T-peel strength between the coated side and uncoated side of the portions of the substrate taken from a roll. Cold seal bonding is measured as T-peel strength between the coated sides of two sections of coated substrate that have been pressed together under pressure of 80 psi for 0.5 seconds.

The test results on the different substrates are reported in Table 1. These test results show none of the substrate rolls exhibited blocking after one month storage at 25° C. while an initial T-peel value bond strength of 300 g/25 mm can be obtained by pressing together cold seal adhesive coated portions of all the substrates. Blocking is considered to have occurred when T-peel strength value exceeds 50 grams/25 mm.

TABLE 1

| Substrate | Bond Strength No aging (g/25 mm) | | Bond Strength with Aging (g/25 mm) | |
|---|---|---|---|---|
| | Blocking | Cold Seal | Blocking | Cold Seal |
| A | 15 | 320 | 16 | 340 |
| B | 18 | 300 | 10 | 340 |
| C | 10 | 540 | 12 | 550 |

TEST METHODS

T-peel strength: Bond strength is measured according to ASTM D1876-72. Briefly, the dry cold seal adhesive coated plastic films are bonded together by application of 80 psi pressure with 0.5 second dwell time at ambient temperature. The T-peel bond is measured immediately on an Instron tensometer with 305 mm/minute speed. The T-peel strength is reported in grams/25 mm.

Coat weight: The dry adhesive coat weight on the substrate is measured according to ASTM D899-51. The coat weight is reported in lb./ream (lb./3000 ft$^2$).

Viscosity: Viscosity of the aqueous dispersions of cold seal adhesive is measured according to ASTM D1084-63, Method A, Zahn cup No. 2. Viscosity is reported in seconds.

Solids content: Solids content of the aqueous dispersions is measured using an Arizona Instrument Model LX-10 solid analyzer. The starting temperature is 60° C. and the highest temperature is 200° C. The solids content is reported in weight percentage.

Glass transition temperature (Tg): The Tg of the dry adhesive is measured by Rheometrics Dynamics Analysis (RDA) method. Its value is obtained from the maximum of the tan δ curve.

Surface energy of substrate: This property is approximately measured by a dyne pen method. Different dyne level markers are obtained from Diversified Enterprises and are used to make the measurements. The surface energy is reported in dynes/cm.

I claim:

1. Sheet material for packaging of comestibles and pharmaceuticals comprising a continuous flexible plastic film having a first surface with energy level above 36 dynes/cm and a second surface with energy level below 32 dynes/cm with said first surface bearing a geometric pattern coating of dry cold seal adhesive consisting essentially of a polyurethane ionomer reaction product of 50–80% polyester polyol, 15–25% aliphatic diisocyanate and 3–6% dimethylol propionic acid neutralized with a base, said reaction product possessing a $T_g$ of between about –20° to 5° C.

2. The sheet material of claim 1 wherein said cold seal adhesive coating is the dried residue from application to said film of an aqueous dispersion having a Zahn Cup #2 viscosity between 16–40 seconds containing 30 to 50 percent solids content of a polyurethane ionomer reaction product of 50–80% polyester polyol, 15–25% aliphatic diisocyanate and 3–6% dimethylol propionic acid neutralized with a base selected from tertiary amines and alkali metal hydroxides, said reaction product possessing a $T_g$ of between about –20° to 5° C.

3. The sheet material of claim 2 wherein said pattern consists of stripes of said cold-seal adhesive.

4. The sheet material of claim 3 wherein said stripes form a plurality of separate rectangles spaced apart longitudinally along said film.

5. A non-blocking roll of sheet material for packaging of comestibles and pharmaceuticals comprising a continuous flexible plastic film having a first surface with energy level above 36 dynes/cm and a second surface with energy level below 32 dynes/cm with said first surface bearing a geometric pattern coating of dry cold seal adhesive consisting essentially of a polyurethane ionomer reaction product of 50–80% polyester polyol, 15–25% aliphatic diisocyanate and 3–6% dimethylol propionic acid neutralized with a base, said reaction product possessing a $T_g$ of between about –20° to 5° C.

* * * * *